United States Patent [19]

Chipman et al.

[11] Patent Number: 4,660,151

[45] Date of Patent: Apr. 21, 1987

[54] MULTICOMPONENT QUANTITATIVE ANALYTICAL METHOD AND APPARATUS

[75] Inventors: Russell A. Chipman, Tucson, Ariz.; Robert J. Obremski, Yorba Linda, Calif.; Christopher W. Brown, Saunderstown, R.I.

[73] Assignee: Beckman Instruments, Inc., Fullerton, Calif.

[21] Appl. No.: 533,833

[22] Filed: Sep. 19, 1983

[51] Int. Cl.[4] .................. G06F 15/347; G01J 3/12; G01N 21/25

[52] U.S. Cl. ................... 364/498; 364/576; 356/326

[58] Field of Search .............. 364/497, 498; 356/319-334

[56] References Cited

U.S. PATENT DOCUMENTS 4,093,991 6/1978 Christie, Jr. et al. ........... 364/498 X
4,171,913 10/1979 Wildy et al. .................... 364/498 X

OTHER PUBLICATIONS

Koenig: Computerized Infrared Spectroscopy via Fourier Transform Techniques, American Laboratory, vol. 6, No. 9, Sep. 1974, pp. 9, 11, 12, 14–16.
Zweibaum: Fully Integrated On-Line Process Control System Employing Microcomputer Based IR Spectrometer Proceedings of the Society of Photo-Optical Instrumentation Engineers, SPIE, vol. 170, Jan. 1979, pp. 91–106.
Chen, J-y. T. and Gardner, A. M., "Multicomponent Analyses of PCBs by FTIR Spectroscopy", American Laboratory, Mar. 1983, pp. 26–33.
Sparks, D. T., Lam, R. B. and Isenhour, T. L., "Quantitative Gas Chromatography/Fourier Transform Infrared Spectrometry with Integrated Gram–Schmidt Reconstruction Intensities", Anal. Chem., 1982, 54, pp. 1922–1926.
Koenig, J. L. and Rodriquez, J. M. T., "Factor Analysis and Fourier Transform Infrared Spectra of Compatible Blends of Polyphenylene Oxides and Polystyrene", Applied Spectroscopy, vol. 35, No. 6, 1981, pp. 543–548.
Malinowski, E. R. and Howery, D. G., *Factor Analysis in Chemistry*, Wiley & Sons, 1980.
Small, G. W., Rasmussen, G. T., and Isenhour, T. L., "An Infrared Search System Based on Direct Comparison of Interferograms", Applied Spectroscopy, vol. 33, No. 5, 1979, pp. 444–450.
Antoon, M. K., D'Esposito, L. and Koenig, J. L., "Factor Analysis Applied to Fourier Transform Infrared Spectra", Applied Spectroscopy, vol. 33, No. 4, 1979, pp. 351–357.
Rasmussen, G. T. and Isenhour, T. L., "Principal Component Analysis of the Infrared Spectra of Mixtures", Analytica Chimica Acta, vol. 103, 1978, pp. 213–221.
Antoon, M. K., Koenig, J. H. and Koenig, J. L., "Least-Squares Curve-Fitting of Fourier Transform Infrared Spectra with Applications to Polymer Systems", Applied Spectroscopy, vol. 31, No. 6, 1977, pp. 518–524.
Weiner, P. H., "Solve Problems via Factor Analysis", Chemtech, May 1977, pp. 321–328.
Malinowski, E. R., "Theory of Error in Factor Analysis", Analytical Chemistry, vol. 49, No. 4, Apr. 1977, pp. 606–612.
Bulmer, J. T. and Shurvell, M. F., "Factor Analysis as a Complement to Band Resolution Techniques, I, The Method and its Application to Self-Association of Acetic Acid", Journal of Physical Chemistry, vol. 77, 1973, pp. 256–262.
Hugus, Jr., Z. Z., "The Determination of the Number of Species Present in a System: A New Matrix Rank Treatment of Spectrophotometric Data", Journal of Physical Chemistry, vol. 75, No. 19, 1971, pp. 2954–2957.
Blackburn, J. A., "Computer Program for Multicomponent Spectrum Analysis Using Least-Squares Method", Analytical Chemistry, vol. 37, No. 8, Jul. 1965, pp. 1000–1003.
Malinowski, E. R., "Determination of the Number of Factors and the Experimental Error in a Data Matrix", Analytical Chemistry, vol. 49, No. 4, Apr. 1977, pp. 612–617.

*Primary Examiner*—Felix D. Gruber
*Attorney, Agent, or Firm*—William H. May; Gary T. Hampson; Steven R. Markl

[57] ABSTRACT

A multicomponent quantitative analytical method and apparatus wherein the method includes the steps of and the apparatus is capable of performing steps of obtaining a plurality of calibration spectra, transforming the calibration spectra using a transform with orthogonal basis vectors, obtaining a calibration matrix relating the transform spectra to concentrations of analytes in the calibration samples, obtaining a spectrum for an unknown sample, transforming the unknown sample spectrum, and relating the transformed unknown sample spectrum to the calibration matrix to thereby determine the concentration of analytes in the unknown sample.

11 Claims, 9 Drawing Figures

MULTICOMPONENT QUANTITATIVE ANALYTICAL METHOD AND APPARATUS

FIELD OF THE INVENTION

The present invention relates generally to the field of spectral analysis and in particular to a method and apparatus useful for quantitative analysis of spectral data. The method and apparatus of the present invention finds particular application to the quantitative analysis of spectral data obtained from a sample comprising a plurality of components or analytes, that is, a multicomponent sample.

BACKGROUND OF THE INVENTION

Spectral analysis finds wide application in identifying and quantitating analytes in a sample. One particular form of spectral analysis measures the amount of electromagnetic radiation which is absorbed by a sample. For example, an infrared spectrophotometer directs a beam of infrared radiation at or through a sample and measures the amount of infrared radiation absorbed by the sample throughout some range of radiation wavelengths. An absorbance spectrum may then be plotted which relates sample absorbance to radiation wavelength. The overall shape of the absorbance spectrum, including the wavelengths and relative magnitudes of peak absorbance values, is characteristic of the particular analytes in the sample and thus may be used to attempt to identify, generally or particularly, the analytes.

Moreover, the absorbance spectrum may also be used in an attempt to quantitate the concentrations of each analyte in the sample. In accordance with a well known relationship expressed by Beer's Law, the absorbance of an analyte in a sample is essentially proportional to the concentration of the analyte in the sample. Where an absorbance spectrum represents the absorbance of a single analyte in a sample, the concentration of the analyte may be easily determined by comparing the sample absorbance at at least one wavelength to the absorbance of a sample at the same wavelength containing a known concentration of the analyte.

The most usual analytical application, however, involves the spectral analysis of a sample containing a plurality of analytes, that is, a multicomponent sample. In multicomponent analysis, Beer's Law still applies and the observed absorbance spectrum for the multicomponent sample is considered to be substantially equal to the sum of the individual absorbance spectra for each of the analytes or components in the sample.

Methods and apparatus for the quantitation of analyte concentrations in multicomponent samples are known in the art. The prior methods and apparatus each require that absorbance spectra for a plurality of calibration samples be obtained. The calibration samples each include various predetermined concentrations of analytes which are thought to be the same analytes present in unknown concentrations in an unknown sample. A plurality of absorbance values at predetermined identical wavelengths are determined on each of the calibration spectra providing a set of absorbance values for each spectra. The sets are arranged as, for example, columns in an absorbance matrix, A. The known concentrations of the analytes also form a set of values for each calibration sample. All of the sets of concentration values for the calibration samples are arranged as columns in a concentration matrix, C. Using matrix mathematics, the absorbance matrix A is related to the concentration matrix C by a constant matrix K in accordance with the following expression:

$$A = K*C \qquad \text{Equation 1}$$

where "*" represents matrix multiplication. Using matrix mathematics, the constant matrix K is determined and the inverse thereof, P, is also determined, that is, $P*A = P*K*C$, or $C = P*A$ An absorbance spectrum is also determined for an unknown sample. Absorbance values are selected from the unknown sample spectrum at the same wavelengths used to determine absorbance values from the calibration spectra. The unknown sample absorbance values are arranged into a sample matrix S, a vector, and the concentrations of the analytes in the unknown sample may then be determined using the following relationship:

$$P*S = U, \qquad \text{Equation 2}$$

where the vector U should substantially equal the concentrations of the analytes in the unknown sample. As will be apparent to those skilled in the art, a matrix having either one row or one column may be called a "vector", and both "matrix" and "vector" may be used herein for such a matrix.

The method just described has several inherent disadvantages which limit the accuracy of the method and similar methods. The number of absorbance values selected from the calibration spectra and the wavelengths at which the absorbance values are determined influence the accuracy of the method. For example, absorbance values for wavelengths at which the calibration spectra exhibit absorbance peaks may be selected. However, the resulting representation of the calibration spectra is extremely limited and does not provide a detailed representation of such spectra.

In an effort to better represent the absorbance spectra, the number of absorbance values may be increased. However, increased numbers of absorbance values also increases the complexity and the time required to determine the P matrix and to determine the unknown sample concentration vector U. Even with a large number of absorbance values from each absorbance spectrum, the resulting sets of absorbance values still provide only a limited representation of the absorbance spectra.

Another drawback of the method described above is that the measured absorbance spectra may include some high-frequency noise introduced by the measurement method. The absorbance values selected from the spectra, however, will include the high frequency noise, further contributing to inaccurate unknown sample concentration results.

A further difficulty in the method is that it is first necessary to determine a base line for each spectrum to account for background absorbance. The determination of a base line can be somewhat arbitrary and, if improperly or inaccurately accomplished, further diminishes the accuracy of prior art quantitation methods.

The prior art method described above, as well as similar prior methods, include a further disadvantage in that the determination of the unknown sample concentration vector U assumes that the unknown sample includes only the analytes present in the calibration samples. The prior methods include no means for indicating that other analytes may be present in the sample and merely determine analyte concentrations as though only the analytes present in the calibration samples are present in the unknown sample. Consequently, the unknown sample analyte concentrations determined by prior methods and apparatus may be inaccurate and improperly indicate analyte concentrations which actually are not present.

Thus, there is a need for a multicomponent quantitative analytical method and apparatus which overcomes the limitations and disadvantages of prior art methods and apparatus. In particular, there is a need for a method and apparatus which more accurately represents the calibration sample spectra and unknown sample spectrum. There is also a need for a method and apparatus which is less influenced by measurement noise and which obviates the selection of base line to account for background absorbance. There is also a need for a method and apparatus which will indicate that the unknown sample includes analytes other than those present in the calibration samples.

SUMMARY OF THE INVENTION

The present invention provides a multicomponent quantitative analytical method and apparatus which overcomes the limitations and disadvantages described above. A method and apparatus in accordance herewith uniquely and advantageously more accurately represents the calibration and unknown spectra which reduces the influence of high-frequency noise. The present method and apparatus eliminates the need for selection of base lines for the spectra and importantly provides means for indicating when the unknown sample includes analytes other than those present in the calibration samples.

Towards the foregoing ends, a method in accordance herewith includes the steps of, and an apparatus includes means for, obtaining calibration spectra for calibration samples containing known concentrations of selected analytes such that the spectra represent values proportional to concentration. The calibration spectra are each transformed using a transform with orthogonal basis functions. Using the transformed spectra, a multivarient analysis is performed to obtain a reference or calibration matrix relating known concentrations of analytes in the calibration samples to the transformed spectra.

For an unknown sample, an unknown spectrum is determined and the spectrum is transformed using a transform with orthogonal basis functions. Using the transformed unknown spectrum and the calibration matrix, an unknown concentration matrix is determined, thereby completing the quantitative multicomponent analysis of analytes present in the unknown sample.

The method and apparatus may further include determining points related to the calibration and unknown spectra to eliminate or reduce high-frequency noise and deleting a portion of the values present in the transformed spectra to remove or reduce background absorbances present in the calibration and unknown spectra. Furthermore, residual concentration may be determined to find the contribution to the unknown sample spectrum by analytes other than those present in the calibration samples.

DETAILED DESCRIPTION

Figure 1:
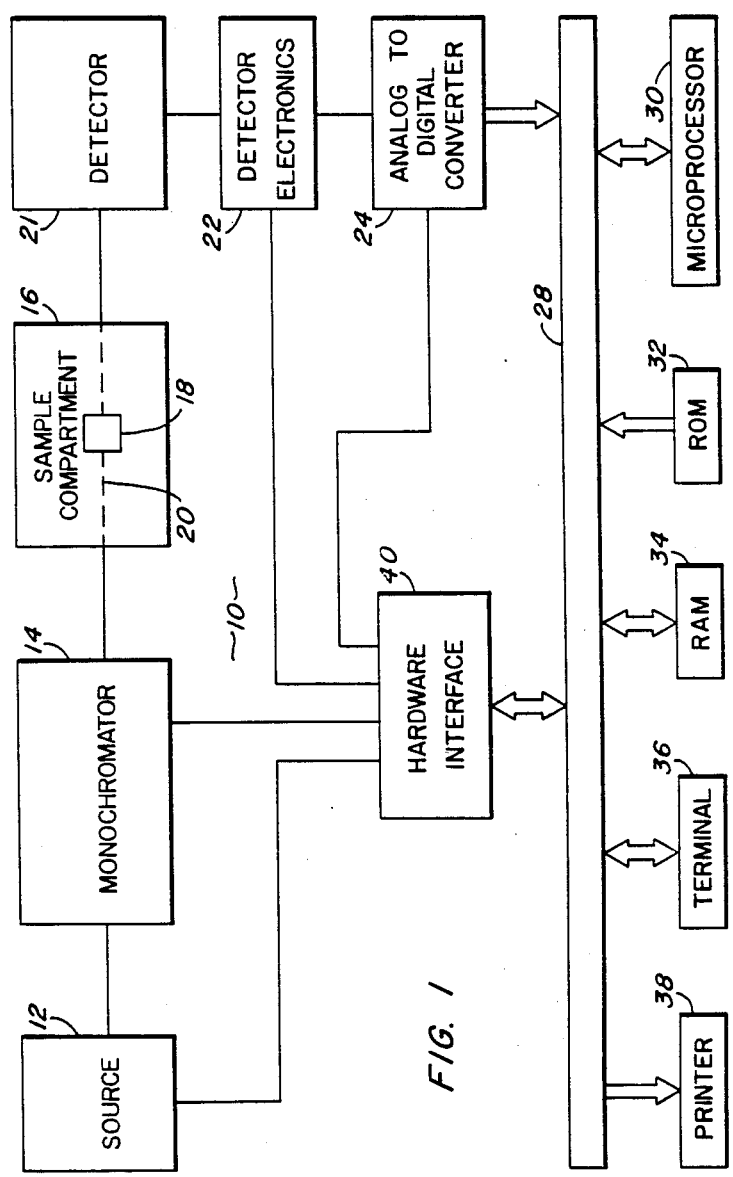
FIG. 1 is a simplified block diagram of a apparatus in accordance with the present invention.

With reference to FIG. 1, apparatus 10 in accordance with the present invention generally comprises elements necessary for obtaining an absorbance spectrum of a sample and further for performing a multicomponent analysis using the absorbance spectrum.

More particularly, the apparatus 10 includes a source 12 which emits infrared radiation that is applied to a monochromator 14. The monochromator 14 selects a relatively narrow band of infrared radiation and directs such radiation to a sample compartment 16. A sample 18 may be placed into the sample compartment 16 such that the sample 18 intercepts a beam 20 of infrared radiation from the monochromator 14. In the embodiment disclosed herein, the sample 18 transmits the infrared radiation in the beam 20 in accordance with the absorbance of the sample 18 at the particular wavelengths of infrared radiation comprising the beam 20. The transmitted radiation is applied to a detector 21 which provides an output proportional to the energy of the transmitted radiation to detector electronics 22.

The detector electronics 22 amplifies and further processes the output of the detector 21 and in turn applies an output proportional to absorbance to an analog-to-digital converter (ADC) 24. The ADC 24 converts the analog output of the detector electronics 22 into a multi-bit digital representation which is in turn applied to a computer system 26.

The computer system 26 is of conventional design and may include an address and data bus 28 which communicates the digital output of ADC 24 to, among other elements, a microprocessor 30. The microprocessor may be, for example, a type 8080A available from INTEL and described in the 1981 Intel Component Data Catalog. The computer system 26 further includes a conventional memory subsystem comprising read-only-memory (ROM) 32 and random-access-memory (RAM) 34 both in communication with the bus 28. An input-output device, such as a terminal 36, may also be in communication with the bus 28, as well as a printer 38 for providing printed results of operations performed by the apparatus 10. A hardware interface 40 of conventional design and in communication with the bus 28 provides an interface between the computer system 26 and the remaining hardware elements of the apparatus 10, such as the source 12, the monochromator 14, the detector electronics 22 and the ADC 24. By means of the hardware interface 40, the microprocessor 30 controls the operation of the apparatus 10. In turn, the operation controlled by the microprocessor 30 may be specified by a user through the terminal 36, thus providing an automated apparatus 10.

The apparatus 10 may be formed from a conventional spectrophotometer modified in accordance with the present invention as is described hereinbelow with respect to the operation of the apparatus 10. The apparatus 10 may comprise, for example, a DU -7 spectrophotomer, a DU -8 spectrophotometer, or a Microlab spectrophotometer, all available from Beckman Instruments, Inc., and all modified to perform as disclosed herein. In particular, such modification may include variations in software stored in the ROM 32, and RAM 34. Such variations cause the microprocessor 30 to, in effect, reconfigure an otherwise conventional spectrophotometer to form the apparatus 10 in accordance with the present invention. The execution of such modifications will be readily apparent to those skilled in the art using the description included herewith, and may include well known and otherwise conventional computer program development techniques. Thus, the computer system 26, including the microprocessor 30, provides structure which corresponds to means for performing various functions.

The operation of the apparatus 10 in accordance with the present invention will first be described in general terms with reference to FIGS. 2-4. Various elements of FIG. 2 will then be described in detail with reference to FIGS. 5-8 including descriptions of alternative embodiments for some elements of FIG. 2.

Figure 2:
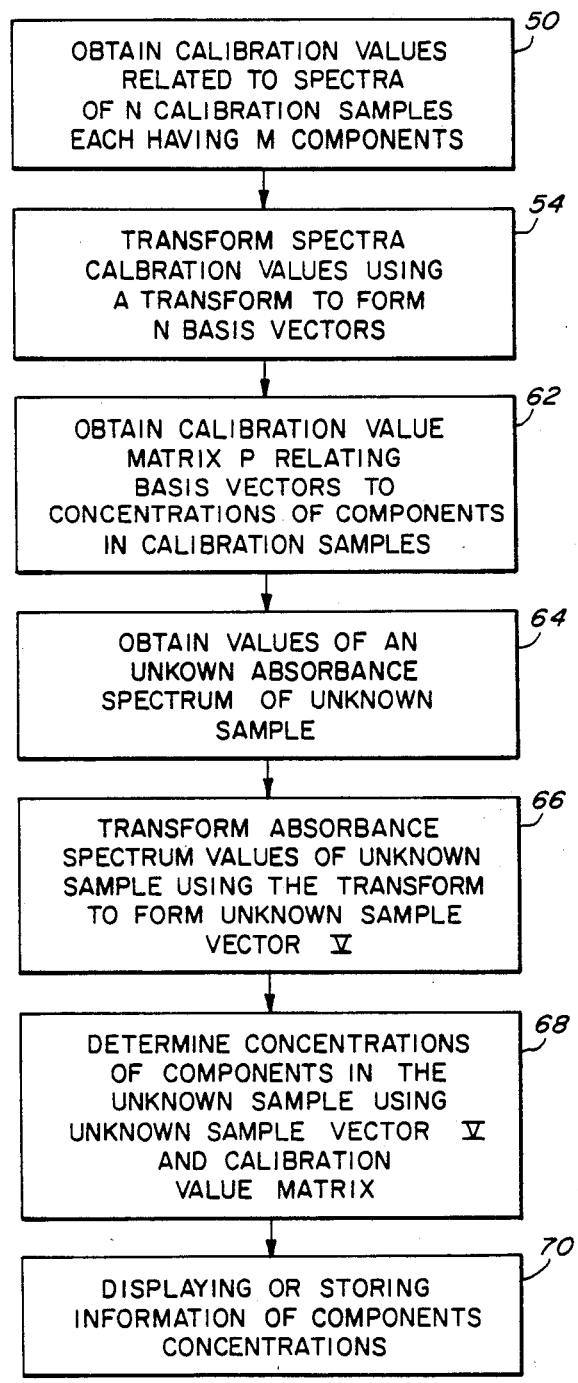
FIG. 2 is a block diagram of a method in accordance with the present invention and performed by the apparatus of FIG. 1.

As seen with reference to FIG. 2, a first step includes determining calibration absorbance spectra for N number of calibration samples, each of the samples having varying concentrations of M components. Each such calibration absorbance spectra may be obtained by operating the apparatus 10 in a well-known fashion. For example, each calibration sample is placed within the sample compartment 16 as the sample 18. The monochromator 14 is then controlled so as to provide a beam of infrared radiation from the monochromator 14 having wavelengths varying over a predetermined range of wavelengths desired for the absorbance spectra being measured, such as about 400 to 4000 wavenumbers. The radiation passing through the sample 18 is detected by the detector 21, processed by the detector electronics 22 and converted to a digital signal by means of ADC 24. The output of the detector 21, which is a signal proportional to transmittance of the sample 18, may be converted, for example, in the detector electronics 22 to a signal proportional to absorbance. As the wavelength of the beam 20 is varied, the ADC 24 is commanded to periodically convert the analog output of the detector electronics 22 to the digital representation which is applied to the bus 28. The microprocessor 30 may then store each digital absorbance value into the RAM 34. Successively stored digital absorbance values together define an absorbance spectrum for the sample 18. As seen in FIG. 3, a typical absorbance spectrum for one calibration sample may appear as shown by curve 52 representing a smoothed version of the individual digital absorbance values stored in the RAM 34.

Figure 3:
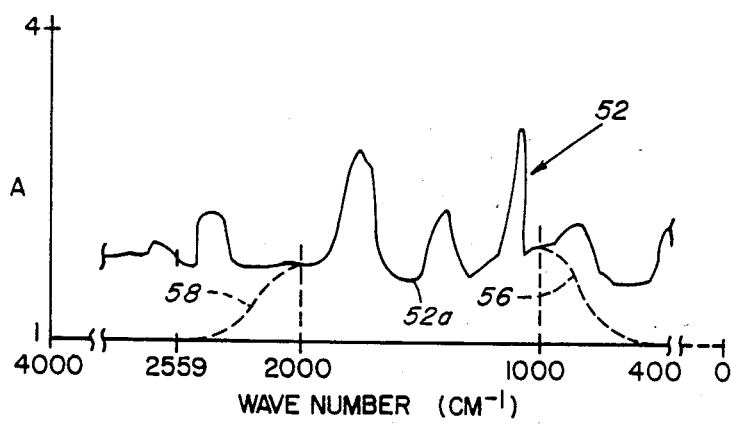
FIG. 3 is an example of an absorbance spectrum obtained by the apparatus of FIG. 1.

With continued reference to FIG. 3, a portion 52a of the spectrum 52 may be selected as a characteristic or "fingerprint" region of the spectrum as, for example, the region between and including wavenumbers 2000 and 1000. Accordingly, the remainder of the spectrum 52 will not be used in the remainder of the steps shown in FIG. 2.

Returning to FIG. 2, a next step 54 includes transforming the calibration absorbance spectra for each of the calibration samples. Advantageously, the transform selected is one with orthogonal basis functions, that is, the transform selected transforms each absorbance spectrum into vectors in a function space whose coordinate axes may represent a complete set of orthonormal functions. Examples of such function spaces are those constructed from Legendre polynomials, Fourier series and transforms, and Chebyshev polynomials. In the embodiment disclosed herein, the Fourier transform is used to transform each of the calibration absorbance spectra into corresponding vectors.

In the embodiment disclosed herein, the Fourier transform is implemented in the apparatus 10 as a fast Fourier transform (FFT) performed by the microprocessor 20. As will be recognized by those skilled in the art, the FFT requires some integer power of two ($2^x$) input data points. In the embodiment disclosed herein, 256 data points are used for the FFT. To obtain the 256 data points, the portion 52a of the spectrum 52 may first be smoothly tapered on either end as shown by dashed segments 56 and 58 to provide a number of points equal to some whole number multiple of the number of input data points for the FFT. For example, the portion 52a may be tapered to provide 2560 points, from and including "wavenumber" 0 to and including wavenumber 2559. In the embodiment disclosed herein, the tapered portions 56 and 58 are tapered using a cosine type function, although simple horizontal extrapolation obtained by extending the portion 52a horizontally from the endpoints thereof could also be used. The 256 data points are then determined such that every tenth point along the portion 52a and the segments 56 and 58 corresponds to a respective data point. Specifically, a weighted average is applied to the points surrounding each such tenth point to thereby produce a respective data point. In the embodiment disclosed herein, the weighted average is a sinc interpolation, that is, the points surrounding each such tenth point (e.g. ±5 points) are decimated by sinc convolution as is well known in the statistical art.

Continuing with the step 54 shown in FIG. 2, the computer system 26 is commanded so as to perform a FFT using the 256 points determined from the portion 52a corresponding to absorbance values and from the tapered segments 56 and 58. Programs performing FFTs are well known in the art and are described, for example, in *The Fast Fourier Transform* by E. Oran Brigham (Prentice-Hall, 1974).

The FFT produces as an output the same number of points as there were input, that is, 256. As seen in FIG. 4, the output of the FFT may be represented as a curve 60 comprising 256 data points. Advantageously, only a portion of the points on the curve 60 between limits $x_1$ and $x_2$ need be used to provide an accurate representation of the absorbance data in the portion 52a of FIG. 3. The selected points together define a calibration vector. In the embodiment disclosed herein, only about 30 to 60 points on the curve 60 need be retained. The limit $x_1$ is selected so as to eliminate or substantially reduce background absorbance but, where necessary, retain broad spectral features which may be characteristic of the portion 52a. In the embodiment disclosed herein, the limit $x_1$ may be offset from zero by about 10 to 120.

Where, for example, broad spectral features are included in the portion 52a and such features are to be retained in performing the spectral analysis of the present invention, $x_1$ would be selected to be greater than but near 10. However, where broad features need not be retained, $x_1$ may be selected to be nearer 120. Those skilled in the spectroscopic art will readily select the particular value for $x_1$ according to the requirements of the analysis being performed.

With $x_1$ selected as just described, $x_2$ will correspondingly be in a range of about 40 to 180. By selecting only a proportion of the curve 60, the number of elements required for performing the remaining steps of the operation shown in FIG. 2 is limited, to thereby simplify the requirements of the computer system 26 by decreasing the amount of memory required in the computer system 26 and increasing the speed with which the operation of FIG. 2 may be performed. Moreover, determining the FFT input data points as described above and limiting the FFT to 256 data points eliminates or substantially reduces high-frequency noise within the spectrum segment 52a. Also, by deleting the points on the curve 60 below the limit $x_1$, background absorbance is eliminated or substantially reduced, thus eliminating the requirement of base line determination required in prior method as described above.

As just described, the method and apparatus of the present invention contemplate determining FFT input data points related to the portion 52a and the segments 56 and 58 so as to reduce or substantially eliminate high frequency noise within the spectrum portion 52a. Those skilled in the art will recognize that such a procedure is equivalent to performing a FFT of all points along the portion 52a and subsequently deleting the higher frequency terms from the output of the FFT. However, such an equivalent procedure requires that the FFT be performed with a larger number of data points, requiring increased processing time and memory requirements. In either case, terms are omitted from the transformed spectra which correspond to values representing high-frequency noise.

With reference again to FIG. 2, each of the calibration absorbance spectra are processed as just described to provide a total of N sets of transformed spectra. The data associated with each transformed spectrum, that is, the points between limits $x_1$ and $x_2$ for each curve similar to the curve 60, can be considered a calibration vector. Thus, the results obtained by step 54 in FIG. 2 include N calibration vectors in a function space representing calibration absorbance spectra in a manner heretofore unknown in the art.

Figure 4:
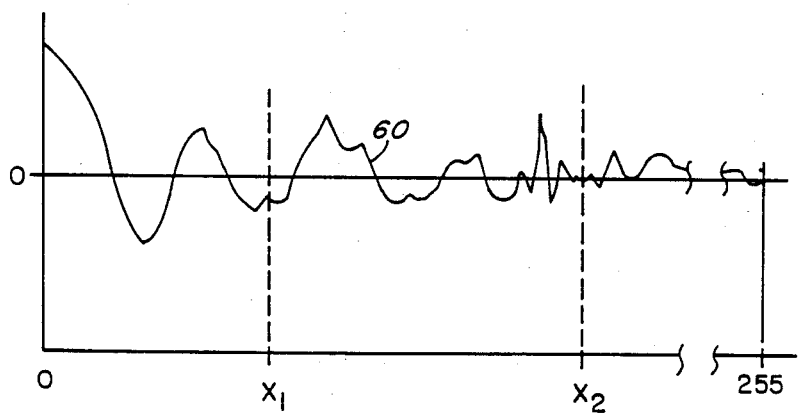
FIG. 4 is a representation of a transformed absorbance spectrum in accordance with the present invention.

In forming the calibration vectors as just described above in step 54, it may be desirable to resample the output data from the FFT shown by curve 60 in FIG. 4 such that a total number of 30 to 60 elements form each calibration vector but the selected elements are selected, for example, from every two points along the curve 60. Such resampling reduces redundancies and provides a more unique data set forming each of the calibration vectors of step 54.

In a next step 62 (FIG. 2), a calibration matrix is determined which relates the calibration vectors to the concentrations of the components in the calibration samples. As is described more fully hereinbelow, such a determination may be performed using multivarient analysis such as principle factor analysis, although other forms of multivarient analysis may be used as is also described.

Continuing with FIG. 2, once the calibration matrix is formed, an absorbance spectrum for an unknown sample is then determined. The unknown sample absorbance spectrum may be measured as described above for determining the absorbance spectrum 52 shown in FIG. 3. The unknown sample absorbance spectrum is processed in an identical fashion as described above for the calibration spectra. A characteristic or fingerprint portion of the unknown sample absorbance spectrum is selected and, as shown in a step 66, the selected portion of the unknown absorbance spectrum is transformed using the same transformation employed in step 54. In the embodiment herein, a Fourier transformation is employed and preferably implemented by means of a FFT, again yielding the same number of output data points as obtained for each transformation performed in step 54. The resulting output points from the FFT of the unknown absorbance spectrum are trunkated or limited as described previously for the curve 60 in FIG. 4 so as to provide an unknown sample vector V. The sample vector V has the same number of elements as the calibration vectors developed in step 54.

Figure 6:
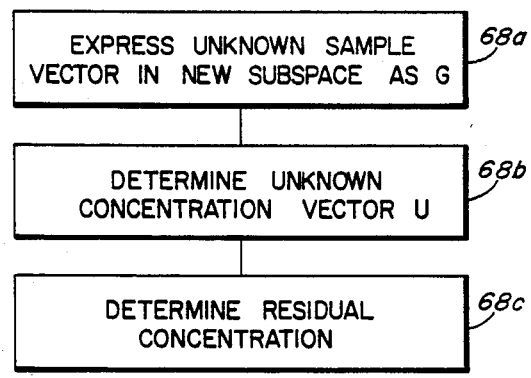
FIG. 6 is a block diagram illustrating detailed substeps step 68 of the block diagram of FIG. 2.

In a last step 68 and as is described more fully hereinbelow with reference to FIG. 6, the concentrations of the components or analytes in the unknown sample are determined using the unknown sample vector and the calibration matrix. Further, a residual concentration vector may be determined and may be used to provide an indication of a proportion of the unknown absorbance spectrum which cannot be accounted for by the calibration spectra, that is, a residual. The residual is indicative of the presence of other components or analytes in the unknown sample.

As described previously, step 62 shown in FIG. 2 includes multivarient analysis which defines a calibration matrix. In the embodiment disclosed herein, eigenanalysis is preferably used to determine a calibration matrix P for use in equation 2 as set out hereinbefore. Eigenanalysis is a wellknown analytical method and is described, for example, in *Factor Analysis In Chemistry* by Malinowski and Howery (Wiley-Interscience, 1980).

Figure 5:
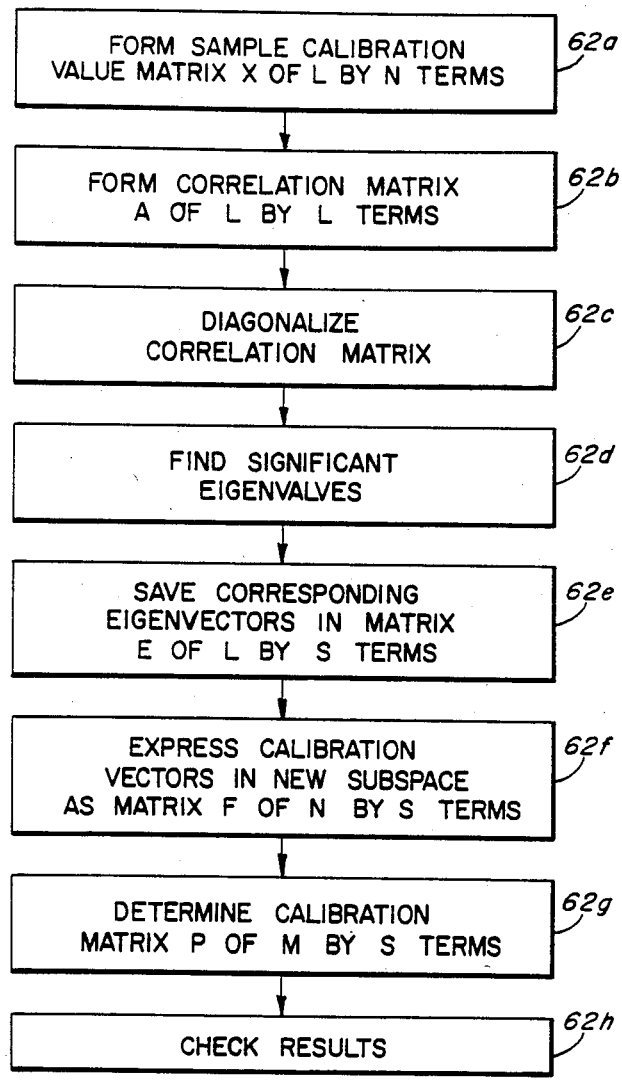
FIG. 5 is a block diagram illustrating detailed substeps for step 62 of the method illustrated in FIG. 2.

The particular method of eigenanalysis used in step 62 is shown in diagramatic form in FIG. 5. As there depicted, a first substep 62a includes forming a calibration sample matrix X of L (rows) by N (columns) terms, where L is the number of elements in each calibration vector and N is the number of calibration samples and thus the number of calibration vectors. A correlation matrix A is formed (step 62b) in accordance with the following:

$$A = X * X^T \qquad \text{Equation 3}$$

where $X^T$ is the transpose matrix of the calibration sample matrix X. The resulting correlation matrix A is a matrix of L by L terms.

In step 62c, the correlation matrix A is diagonalized in a conventional fashion such as by the method of Jacobi or other suitable methods as taught, for example, in *Matrix Computation for Engineers and Scientists* by Alan Jennings (Wiley-Interscience 1977), pages 250–255. The diagonalization yields eigenvalues along the resulting matrix diagonal and also determines the corresponding eigenvectors. Of the eigenvalues appearing in the diagonalized matrix, significant eigenvalues are selected (step 62d), which may be, for example, the eigenvalues greater than about one percent of the maximum eigenvalue determined. For each significant eigenvalue, the corresponding eigenvectors are saved in a matrix E of L by S terms, (step 62e), where S is the number of significant eigenvalues (and thus eigenvectors) determined in step 62d.

In a next step substep 62f, the significant eigenvector matrix E is used to transform or express the calibration vectors into the new eigenvector subspace as a reduced matrix F as follows:

$$F = X^T * E, \qquad \text{Equation 4}$$

where the F matrix is N by S terms. With the matrix F found as in step 62f, the calibration matrix P is determined (step 62g) according to the following:

$$P = C^T * F * (F^T * F)^{-1}, \qquad \text{Equation 5}$$

where C is a N by M concentration matrix for M components and N calibration samples. The P matrix is a M by S matrix. With the calibration matrix P determined, the results may be checked according to the following:

$$P * F^T = C_c, \qquad \text{Equation 6}$$

as shown in step 62h, where $C_c$ is a calculated concentration matrix. Thus, the multivarient analysis procedure of FIG. 5 determines a calibration matrix P which may be used as described below to determine the concentrations of M components or analytes in an unknown sample.

The calibration matrix P may also be checked to determine if intercept correction is required due to deviation of the experimental data from the relationship expressed by Beer's Law. Remembering that the F matrix is of N by S terms, one additional row, N+1, is added to the F matrix, each element in such row being set equal to 1. The new matrix may be designated F hat, and written $\hat{F}$. Using the C matrix described above, a new P matrix having one additional column, S+1, is determined, and may be designated P hat ($\hat{P}$). A new calculated concentration matrix $C_c$ hat is determined using the P hat and F hat matrices according to Equation 6. A conventional and well known statistical F-test may then be performed to compare the C, $\hat{C}_c$, and $C_c$ hat matrices and determine if the difference between the P and P hat matrices is significant. If so, the P hat matrix is used for the following steps.

With the calibration P matrix determined as just described in FIG. 5, the steps 64 and 66 of FIG. 2 are performed to provide an unknown sample vector V as described above. In step 68, shown in more detail in FIG. 6, the unknown sample vector V is expressed in the new subspace as a new vector G (step 68a) in accordance with the following:

$$G = E^T * V, \qquad \text{Equation 7}$$

where the matrix $E^T$ is the transpose matrix of the significant eigenvector matrix E and the matrix V is the unknown sample vector processed and modified as described previously in step 66 of FIG. 2.

An unknown concentration vector U is then determined in accordance with the following:

$$U = P * G, \qquad \text{Equation 8}$$

resulting in a vector of M elements corresponding to the number of components contained in the calibration samples. Each of the elements represents the concentration of the corresponding component in the unknown sample. As will be apparent to those skilled in the art, the G vector as determined by Equation 7 has S elements. Consequently, if intercept correction is required as discussed above and the P hat matrix has been extended to S+1 columns, then the G vector will also be extended by one element, set equal to 1.

Figure 6A:
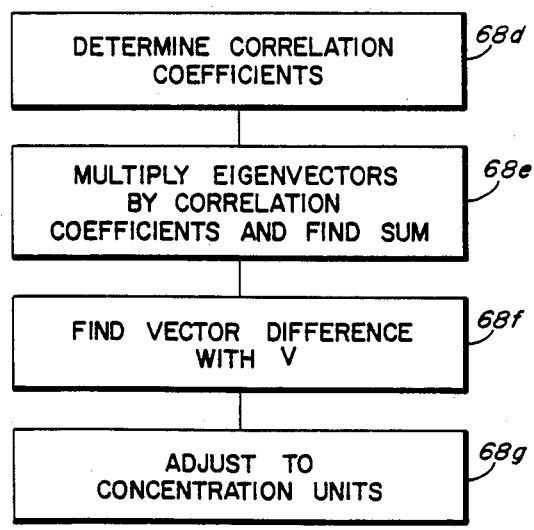
FIG. 6A is a block diagram illustrating substeps for step 68a of the block diagram of FIG. 6.
Figure 7:
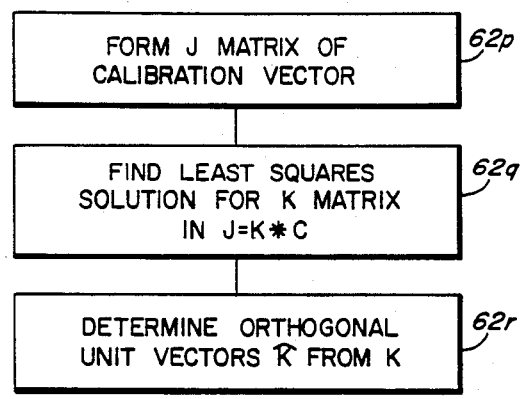
FIG. 7 is a block diagram showing detailed steps of another form of multivarient analysis which may be used to implement step 62 of FIG. 2; and, FIG. 8 is a block diagram illustrating detailed substeps for step 68 of the method of FIG. 2 utilizing the alternative multivarient analysis technique illustrated in FIG. 7.

Although the unknown concentrations of the components in the unknown sample are now determined, it is possible that components other than the components M in the calibration samples may be present in the unknown sample. Therefore, a residual concentration may be determined in order to find the proportion of the absorbance measured for the unknown sample which is contributed by components other than those present in the calibration samples. As one example of steps for determining residual concentration, first find the correlation coefficient k, where k is less than or equal to 1 and greater than or equal to −1, of each of the eigenvectors with the unknown concentration vector V (step 68d, FIG. 6A). Then, multiply each of the eigenvectors by the respective correlation coefficients and form the vector sum of the results (step 68e). Find the vector difference between such vector sum and the unknown sample vector V (step 68g). The vector difference may then be adjusted to concentration units (step 68g) by multiplying by the euclidean length of the vector U and dividing by the euclidean length of the sample vector V. The result indicates the residual concentration.

Although eigenanalysis has been described above as the form of multivarient analysis used in step 62 of FIG. 2, those skilled in the art will appreciate that other forms of multivarient analysis may also be utilized. For example, a method employing Grahm-Schmidt orthogonalization may be used.

In performing such a method, a J matrix (step 62p, FIG. 7) is formed using the calibration vectors obtained from step 54 of FIG. 2. The J matrix has N columns and a number of rows equal to the number of values obtained from the transformation performed in step 54 of FIG. 2. The matrix J may be related to the concentration matrix C by the following relationship:

$$J = K * C, \qquad \text{Equation 9}$$

where the concentration matrix C has N columns and M rows and the constant matrix K has M columns and N rows. As shown in step 62q, a method of least squares is used to solve for the elements in the matrix K.

With the matrix K determined, orthogonal unit vectors in a matrix K hat (shown in step 62r as $\hat{K}$) are determined using the Grahm-Schmidt orgthogonalization as is well known in the art and as described in, for example, *Mathematical Methods for Physicists*, second addition, George Arfken (Academic Press, New York, 1970), at page 437.

Figure 8:
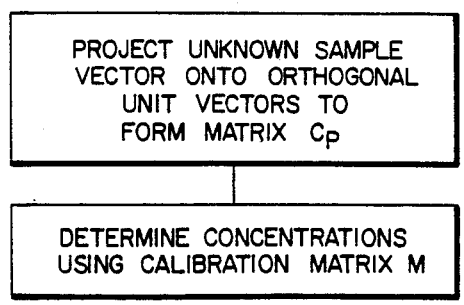

With the orthogonalized K hat matrix determined, the steps 64 and 66 of FIG. 2 may then be performed. The determination of the concentrations of the components in the unknown sample of step 68 in FIG. 2 may be performed. As shown in FIG. 8, the unknown sample vector V is projected onto the orthogonal unit vectors to form a matrix $C_p$ according to the following:

$$C_p = V \cdot \hat{K}. \qquad \text{Equation 10}$$

The concentrations of the components in the unknown sample are then related as follows:

$$K*C = K\text{ hat}*C_P \qquad \text{Equation 11}$$

Solving for matrix C, $$C = (K^T*K)^{-1}*K^T*K \text{ hat}*C_p \qquad \text{Equation 12}$$

The terms $(K^T*K)^{-1}*K^T*K$ hat may be represented as a calibration matrix M whereupon equation 11 becomes:

$$C = M*C_p \qquad \text{Equation 13}$$

Thus, it is seen that although eigenanalysis is prefered, other forms of multivarient analaysis may be used with the present invention.

Having described one embodiment of the present invention, variations and modifications thereof falling within the scope of the appended claims will be apparent to those skilled in the art. For example, although the embodiment of FIG. 1 employs a monochromator 14, it will be recognized that the present invention is applicable to other forms of spectrophotometers, such as those using interferometers or polychromators with diode arrays.

What is claimed:

1. A multicomponent quantitative analytical method for use with an analytical instrument comprising the steps of:
   obtaining calibration values related to spectra for a select number of calibration samples containing predetermined concentrations of selected analytes such that information regarding spectra values proportional to the concentrations of the selected analytes is determined;
   performing a transformation of the spectra calibration values using a transform to obtain orthogonal basis vectors;
   performing a multivariate analysis to obtain a calibration value matrix relating known concentrations of analytes in the calibration sample to the transformed spectra calibration values;
   obtaining values of an unknown spectrum for a sample containing unknown concentrations of analytes;
   performing a transformation of the values of the unknown spectrum using said transform having the property of orthogonality;
   determining the concentrations of the analytes in the sample using the transformed values of the unknown spectrum and the calibration value matrix; and
   displaying or storing information of the concentrations of the analytes.

2. A method is defined in claim 1 additionally comprising the step of excluding from the transformed spectra values terms corresponding to values representing high frequency noise following the step of transforming the calibration values.

3. A method is defined in claim 1 additionally comprising the step of excluding from the transformed spectra values terms corresponding to values representing high frequency noise following the step of transforming the values of the unknown spectrum.

4. A method is defined in claim 1 additionally comprising the step of excluding a portion of the transformed spectra values corresponding to background absorbance following the step of transforming the calibration values.

5. A method is defined in claim 1 additionally comprising the steps of excluding a portion of the transformed spectra values corresponding to background absorbance following the step of transforming the values of the unknown spectra.

6. A method is defined in claim 1 additionally comprising the step of selecting a group of basis vectors on which to perform multivariate analysis in accordance with a predetermined selection function following the step of transforming the calibration values.

7. A method is defined in claim 6 additionally comprising the step of selecting a group of basis vectors using said predetermined selection function for use in relation to the calibration value matrix to determine concentration, following the step of transforming the values of the unknown spectra.

8. A multicomponent quantitative analytical apparatus comprising:
   a first means for obtaining calibration values related to spectra for a select number of calibration samples containing predetermined concentrations of selected analytes such that information regarding spectra values proportional to the concentrations of the selected analytes is determined and;
   for obtaining values of an unknown spectrum for a sample containing unknown concentrations of analytes;
   a second means receiving information signals from said first means, for transforming the calibration values using a transform to obtain orthogonal basis vectors and
   for performing a multivariate analysis to obtain a calibration value matrix relating known concentrations of analytes in the calibration sample to the transformed spectra calibration values and
   for performing a transformation of the values of the unknown spectrum using said transform having the property of orthogonality and
   for determining the concentrations of the analytes in the sample using the transformed values of the unknown spectrum and the calibration value matrix; and
   a third means for displaying or storing information of the concentrations of the analytes.

9. An apparatus as in claim 8 wherein said second means additionally includes means for excluding from the transformed spectra values terms corresponding to values representing high frequency noise.

10. An apparatus as in claim 8 for in said second means additionally includes means for excluding a portion of the transformed spectra values corresponding to background absorbance.

11. An apparatus as in claim 8 wherein said second means additionally includes means for selecting a group of basis vectors from the orthogonal basis vectors obtained through transforming the calibration values or the values of an unknown spectrum in accordance with a predetermined selection function such that said select group of basis vectors may be used in relating the calibration value matrix with transformed values of the unknown spectrum to determine concentrations of the analytes.

* * * * *